(12) United States Patent
Wu et al.

(10) Patent No.: US 12,347,062 B2
(45) Date of Patent: Jul. 1, 2025

(54) METHODS TO IMPROVE THE PERCEPTUAL QUALITY OF FOVEATED RENDERED IMAGES

(71) Applicant: Magic Leap, Inc., Plantation, FL (US)

(72) Inventors: Bing Wu, Davie, FL (US); Bjorn Nicolaas Servatius Vlaskamp, Seattle, WA (US); Howard Russell Cohen, Weston, FL (US); Jose Felix Rodriguez, Hialeah, FL (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 18/439,296

(22) Filed: Feb. 12, 2024

(65) Prior Publication Data

US 2024/0185380 A1   Jun. 6, 2024

Related U.S. Application Data

(63) Continuation of application No. PCT/US2022/040267, filed on Aug. 12, 2022.

(60) Provisional application No. 63/232,787, filed on Aug. 13, 2021.

(51) Int. Cl.
*G06F 3/01* (2006.01)
*G06T 3/40* (2006.01)
*G06T 15/10* (2011.01)

(52) U.S. Cl.
CPC .............. *G06T 3/40* (2013.01); *G06F 3/013* (2013.01); *G06T 15/10* (2013.01)

(58) Field of Classification Search
CPC . G06F 3/011; G06F 3/013; G06T 3/40; G06T 15/10
See application file for complete search history.

(56) References Cited

U.S. PATENT DOCUMENTS

| 11,064,387 B1 | 7/2021 | Movshovich et al. |
| 2018/0252913 A1* | 9/2018 | Tardif ................ G02B 27/0093 |
| 2019/0043167 A1* | 2/2019 | Steyskal ............ G02B 27/0172 |

(Continued)

OTHER PUBLICATIONS

Haskins et al., "Active vision in immersive, 360° real-world environments. Scientific reports, 10(1), 14304.", https://doi.org/10.1038/s41598-020-71125-4, 2020, 11 pages.

(Continued)

*Primary Examiner* — Lisa S Landis
(74) *Attorney, Agent, or Firm* — KILPATRICK TOWNSEND & STOCKTON LLP

(57) ABSTRACT

A method of generating foveated rendering using temporal multiplexing includes generating a first spatial profile for an FOV by dividing the FOV into a first foveated zone and a first peripheral zone. The first foveated zone will be rendered at a first pixel resolution, and the first peripheral zone will be rendered at a second pixel resolution lower than the first pixel resolution. The method further includes generating a second spatial profile for the FOV by dividing the FOV into a second foveated zone and a second peripheral zone, the second foveated zone being spatially offset from the first foveated zone. The second foveated zone and the second peripheral zone will be rendered at the first pixel resolution and the second pixel resolution, respectively. The method further includes multiplexing the first spatial profile and the second spatial profile temporally in a sequence of frames.

20 Claims, 13 Drawing Sheets

(56) References Cited

U.S. PATENT DOCUMENTS

2020/0051207 A1    2/2020  Ogasawara
2020/0082794 A1*   3/2020  Sanders ................. G06F 3/012
2021/0174768 A1    6/2021  Jarvenpaa et al.

OTHER PUBLICATIONS

PCT/US2022/040267, "International Preliminary Report on Patentability", Feb. 22, 2024, 10 pages.
PCT/US2022/040267, "International Search Report and Written Opinion", Dec. 30, 2022, 13 pages.
PCT/US2022/040267, "Invitation to Pay Additional Fees and, Where Applicable, Protest Fee", Oct. 26, 2022, 2 pages.
Sprague et al., "Stereopsis is adaptive for the natural environment. Science Advances, 1(4), 1-17.", https://doi.org/10.1126/sciadv.1400254, 2015, 18 pages.
EP22856697.2, "Extended European Search Report", May 14, 2025, 10 pages.
Sajadi et al., "Edge-guided resolution enhancement in projectors via optical pixel sharing", ACM Transactions On Graphics, ACM, NY, US, vol. 31, No. 4, Jul. 1, 2012, XP059139379, ISSN: 0730-0301, DOI: 10.1145/2185520.2185575, Jul. 1, 2012, 12 pages.

* cited by examiner

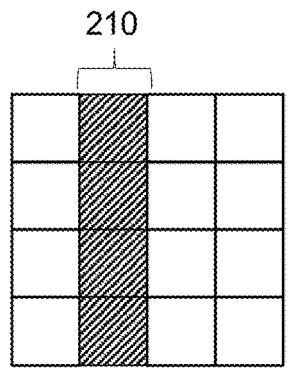

FIG. 2A

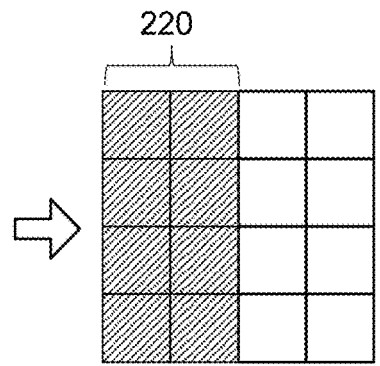

FIG. 2B

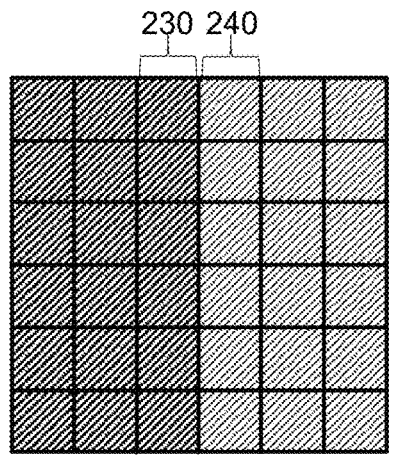

FIG. 2C

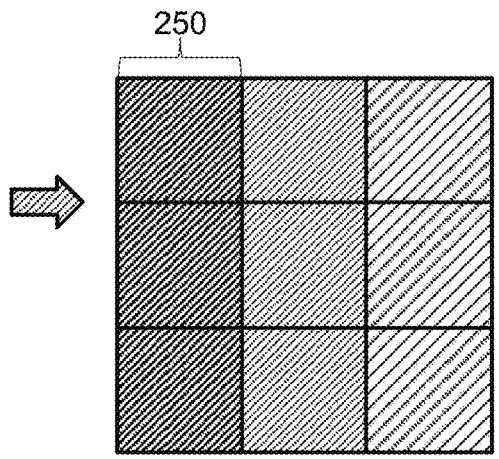

FIG. 2D fox jumps over the lazy dog the quick brown fox jumps over the lazy dog the qu
MPS OVER THE LAZY DOG THE QUICK BROWN FOX JUMPS OVER THE LAZY zy dog the quick brown fox jumps over the lazy dog the quick brown
QUICK BROWN FOX JUMPS OVER THE LAZY DOG THE QUICK fox jumps over the lazy dog the quick brown fox jumps ove
LAZY DOG THE QUICK BROWN FOX JUMPS OVER quick brown fox jumps over the lazy dog the quick b
S OVER THE LAZY DOG THE QUICK BROWN F

FIG. 2E

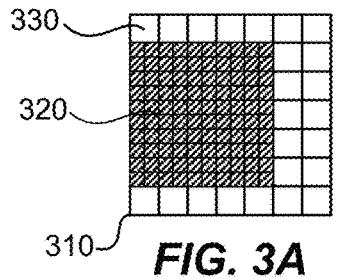
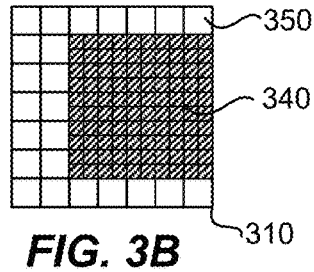
FIG. 3A   FIG. 3B
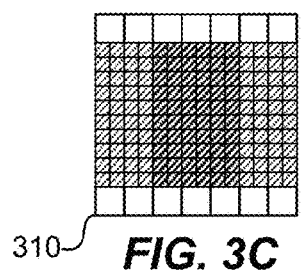
FIG. 3C
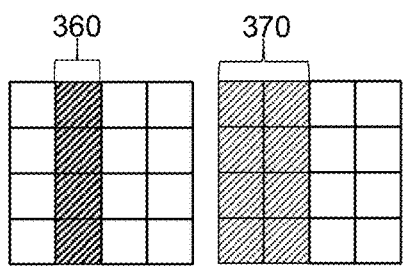
FIG. 3D   FIG. 3E   FIG. 3F
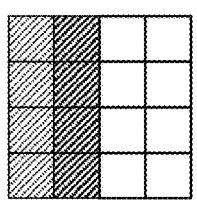
FIG. 3G   FIG. 3H

| Pixel | Byte | Block Name | Value | Description |
|---|---|---|---|---|
| TBD | TBD | Foveated Mode Select | 0x00 | Bit 0: Foveation Mode (0: Full Resolution, 1: Foveation enabled)<br>Bit 1: Red Foveation Enable (0: disabled, 1: enabled)<br>Bit 2: Green Foveation Enable (0: disabled, 1: enabled)<br>Bit 3: Blue Foveation Enable (0: disabled, 1: enabled)<br>Bit [5:4]: Resolution ration for foveation (00: 1:1, 01: 4:1, 10: 9:1, 11: 16:1)<br>Bit [7:6]: Reserved |
| TBD | TBD | Foveated Region Index | 0x01 | Bit [2:0]: Red Foveated Region Start Row[10:8] (0-1999) |
| TBD | TBD | | 0x90 | Bit [7:0]: Red Foveated Region Start Row[7:0] (0-1999) |
| TBD | TBD | | 0x01 | Bit [2:0]: Red Foveated Region Start Column[10:8] (0-1999) |
| TBD | TBD | | 0x90 | Bit [7:0]: Red Foveated Region Start Column[7:0] (0-1999) |
| TBD | TBD | | 0x01 | Bit [2:0]: Green Foveated Region Start Row[10:8] (0-1999) |
| TBD | TBD | | 0x90 | Bit [7:0]: Green Foveated Region Start Row[7:0] (0-1999) |
| TBD | TBD | | 0x01 | Bit [2:0]: Green Foveated Region Start Column[10:8] (0-1999) |
| TBD | TBD | | 0x90 | Bit [7:0]: Green Foveated Region Start Column[7:0] (0-1999) |
| TBD | TBD | | 0x01 | Bit [2:0]: Blue Foveated Region Start Row[10:8] (0-1999) |
| TBD | TBD | | 0x90 | Bit [7:0]: Blue Foveated Region Start Row[7:0] (0-1999) |
| TBD | TBD | | 0x01 | Bit [2:0]: Blue Foveated Region Start Column[10:8] (0-1999) |
| TBD | TBD | | 0x90 | Bit [7:0]: Blue Foveated Region Start Column[7:0] (0-1999) |

*FIG. 9*

METHODS TO IMPROVE THE PERCEPTUAL QUALITY OF FOVEATED RENDERED IMAGES

CROSS-REFERENCES TO RELATED APPLICATIONS

This application is a continuation of International Patent Application No. PCT/US2022/040267, filed Aug. 12, 2022, entitled "METHODS TO IMPROVE THE PERCEPTUAL QUALITY OF FOVEATED RENDERED IMAGES," which claims the benefit of and priority to U.S. Provisional Patent Application No. 63/232,787, filed Aug. 13, 2021, entitled "METHODS TO IMPROVE THE PERCEPTUAL QUALITY OF FOVEATED RENDERED IMAGES," the entire disclosures of which are hereby incorporated by reference, for all purposes, as if fully set forth herein.

BACKGROUND OF THE INVENTION

In human eyes, the fovea is responsible for sharp central vision at the center of gaze. Peripheral vision is vision that occurs away from the center of gaze. The visual acuity is poor for peripheral vision as compared to fovea vision. Foveated rendering (FR) is a rendering technique in which the image resolution, or amount of detail, is higher in a region of an image that corresponds to the fixation point, and lower away from the fixation point. FR can achieve significant reduction in rendering power and bandwidth, which can be advantageous in applications with limited resources, such as virtual reality (VR) and augmented reality (AR).

Some FR techniques involve tracking a viewer's eye gaze in real time using an eye gaze tracker integrated with a VR/AR headset. For a satisfactory viewer experience with FR, eye gaze tracking needs to have sufficiently high accuracy, fast speed, and low latency, which can be difficult to achieve. Some FR techniques do not use eye gaze tracking, and instead use a fixed focal point. Such FR techniques are referred to as fixed FR. For example, assuming that a viewer looks at the center of a display, the field of view (FOV) of the display can be divided into a central zone with maximum resolution, and several peripheral zones with reduced resolutions. Since the viewer may not always look at the center of the display, the viewer experience may be compromised. Other techniques such as content-based FR also do not require eye gaze tracking, but may require heavy computational resources.

Therefore, there is a need in the art for improved FR techniques.

SUMMARY OF THE INVENTION

According to some embodiments, a method of generating foveated rendering using temporal multiplexing includes generating a first spatial profile for an FOV by dividing the FOV into a first foveated zone and a first peripheral zone. The first foveated zone will be rendered at a first pixel resolution, and the first peripheral zone will be rendered at a second pixel resolution lower than the first pixel resolution. The method further includes generating a second spatial profile for the FOV by dividing the FOV into a second foveated zone and a second peripheral zone. The second foveated zone is spatially offset from the first foveated zone. The second foveated zone will be rendered at the first pixel resolution, and the second peripheral zone will be rendered at the second pixel resolution. The method further includes multiplexing the first spatial profile and the second spatial profile temporally in a sequence of frames, so that a viewer perceives images rendered in a region of the first foveated zone that does not overlap with the second foveated zone and/or in a region of the second foveated zone that does not overlap with the first foveated zone as rendered at the first pixel resolution.

According to some embodiments, a method of generating foveated rendering using binocular multiplexing includes generating a first spatial profile for an FOV by dividing the FOV into a first foveated zone and a first peripheral zone. The first foveated zone will be rendered at a first pixel resolution, and the first peripheral zone will be rendered at a second pixel resolution lower than the first pixel resolution. The method further includes generating a second spatial profile for the FOV by dividing the FOV into a second foveated zone and a second peripheral zone. The second foveated zone is spatially offset from the first foveated zone. The second foveated zone will be rendered at the first pixel resolution, and the second peripheral zone will be rendered at the second pixel resolution. The method further includes multiplexing the first spatial profile and the second spatial profile for a left eye and a right eye of a viewer, respectively, so that the viewer perceives images rendered in a region of the first foveated zone that does not overlap with the second foveated zone and/or in a region of the second foveated zone that does not overlap with the first foveated zone as rendered at the first pixel resolution.

According to some embodiments, a method of generating foveated rendering using a combination of temporal multiplexing and binocular multiplexing includes generating a first spatial profile for an FOV by dividing the FOV into a first foveated zone and a first peripheral zone. The first foveated zone will be rendered at a first pixel resolution, and the first peripheral zone will be rendered at a second pixel resolution lower than the first pixel resolution. The method further includes generating a second spatial profile for the FOV by dividing the FOV into a second foveated zone and a second peripheral zone. The second foveated zone is spatially offset from the first foveated zone. The second foveated zone will be rendered at the first pixel resolution, and the second peripheral zone will be rendered at the second pixel resolution. The method further includes generating a third spatial profile for the FOV by dividing the FOV into a third foveated zone and a third peripheral zone. The third foveated zone is spatially offset from the first foveated zone. The third foveated zone will be rendered at the first pixel resolution, and the third peripheral zone will be rendered at the second pixel resolution. The method further includes generating a fourth spatial profile for the FOV by dividing the FOV into a fourth foveated zone and a fourth peripheral zone. The fourth foveated zone is spatially offset from the third foveated zone. The fourth foveated zone will be rendered at the first pixel resolution, and the fourth peripheral zone will be rendered at the second pixel resolution. The method further includes multiplexing the first spatial profile and the second spatial profile for a left eye and a right eye of a viewer, respectively, in odd frames; and multiplexing the third spatial profile and the fourth spatial profile for a left eye and a right eye of a viewer, respectively, in even frames.

The third foveated zone can be spatially offset from the first foveated zone in a first direction, and the fourth foveated zone can be spatially offset from the second foveated zone in a second direction opposing the first direction. The spatial offset between the first foveated zone and the third foveated zone can be dynamically changed in a sequence of frames. The spatial offset between the second foveated zone and the fourth foveated zone can be dynamically changed in a sequence of frames. Each of the first spatial profile, the second spatial profile, the third spatial profile, and the fourth spatial profile can include three sub spatial profiles for each of three primary colors, and wherein at least one of the three sub spatial profiles is to be rendered at the second pixel resolution for an entirety of the FOV. The dynamic changing of the spatial offset between the first foveated zone and the third foveated zone can follow a pattern. The dynamic changing of the spatial offset between the second foveated zone and the fourth foveated zone can follow a pattern.

According to some embodiments, a method of realizing video pipeline implementation of dynamically multiplexed foveated rendering includes rendering a foveated image that includes a foveated zone and a peripheral zone, wherein the foveated zone has a first set of image data and is rendered at a first pixel resolution and the peripheral zone has a second set of image data and is rendered at a second pixel resolution lower than the first pixel resolution. The method further includes packing the first set of image data into a first image block and packing the second set of image data into a second image block. The method also includes generating a control packet that includes rendering information associated with the foveated image, concatenating the control packet with the first image block and the second image block to form a frame, and transmitting the frame to a display unit. The control packet is parsed from the transmitted frame and is decoded to obtain the rendering information. Finally, a display image will be rendered according to the decoded rendering information.

The method can also include time warping the frame prior to transmitting the frame to the display unit. The rendering information associated with the image can include whether an FR mode is enabled, the ratio of downsampling, the indices of the start row, or the start column of the foveated zone. The frame can be transmitted to the display unit via a channel link. The foveated image can be rendered in a graphics processing unit (GPU). The control packet can be generated in a graphics processing unit (GPU). Each of the first set of image data and the second set of image data can include time stamps that improve frame synchronization. Each of the first set of image data and each of the second set of image data can include three subsets of data for each of three primary colors, and wherein at least one of the three subsets of data is to be rendered at the second pixel resolution for an entirety of a FOV.

According to some embodiments, a method of realizing video pipeline implementation of dynamically multiplexed foveated rendering including time warp comprises rendering a foveated image that includes a foveated zone and a peripheral zone, wherein the foveated zone has a first set of image data and is rendered at a first pixel resolution and the peripheral zone has a second set of image data and is rendered at a second pixel resolution lower than the first pixel resolution and generating a control packet that includes rendering information associated with the foveated image. The method further includes time warping the foveated image for movement in viewer's position to form a time warped image and transmitting the time warped image and the control packet to a video processor. The method further includes remapping the time warped image into a foveated region packed data block and a low resolution region packed data block, concatenating the control packet with the foveated region packed data block and the low resolution region packed data block to form a frame, and transmitting the frame to a display unit. Next, the control packet will be parsed from the frame and decoded to obtain the rendering information. The method also includes projecting a display image rendered according to the decoded rendering information.

The method can also include performing a late time warping the time warped image to update content boundaries in the time warped image, wherein the late time warping is based on a latest viewer's pose data of a viewer. The latest viewer's pose data of the viewer can be collected by a wearable device including at least one motion sensor. The time warped image and the control packet can be transmitted to the video processor via a headset link. The display unit can be a spatial light modulator (SLM). The control packet can be generated in a graphics processing unit (GPU). Parsing the control packet from the frame and decoding the control packet can be performed by the display unit.

According to some embodiments, a method of realizing video pipeline implementation of binocularly multiplexed foveated rendering including time warp comprises rendering a first foveated image for the left eye that includes a first foveated zone and a first peripheral zone, wherein the first foveated zone has a first set of image data and is rendered at a first pixel resolution and the peripheral zone has a second set of image data and is rendered at a second pixel resolution lower than the first pixel resolution and rendering a second foveated image for the right eye that includes a second foveated zone and a second peripheral zone, wherein the second foveated zone has a third set of image data and is rendered at a third pixel resolution and the peripheral zone has a fourth set of image data and is rendered at a fourth pixel resolution lower than the third pixel resolution. The method further includes generating a control packet that includes rendering information associated with the first foveated image and the second foveated image, time warping the first foveated image and the second foveated image for movement in a viewer's position to form a first time warped image and a second time warped image, compressing the first time warped image and the second time warped image to form a first compressed image and a second compressed image, and transmitting the first compressed image, the second compressed image and the control packet to a video processor. Next, the method further includes decompressing the first compressed image to a first recovered foveated image, decompressing the second compressed image to a second recovered foveated image, performing a second time warp on the first recovered foveated image and the second recovered foveated image based on the latest viewer's pose data, remapping the first recovered foveated image into a first set of three separate color channels to form a first channeled image, packing the first channeled image with the control packet to form a first frame, and transmitting the first frame to a first display for the left eye, wherein the first display for the left eye parses the control packet from the first frame, decodes the control packet to obtain the rendering information of each of the three separate color channels for the first frame, and saves the rendering information of the first frame in a memory of the first display. For the right eye display, the method includes remapping the second recovered foveated image into a second set of three separate color channels to form a second channeled image, packing the second channeled image with the control packet to form a second frame and transmitting the second frame to a second display for the right eye, wherein the second display for the right eye parses the control packet from the first frame, decodes the control packet to obtain the rendering information of each of the three separate color channels for the second frame, and saves the rendering information of the second frame in a memory of the second display.

The video processor can be a component of a wearable device. The first compressed image and the second compressed image can be transmitted to the video processor via a headset link. The first display and the second display can be liquid crystal on silicon (LCOS) displays. Each of the three separate color channels can have an independent foveated zone or downsampling ratio. Each of the three separate color channels can be sequentially displayed to the viewer. Locations of the first foveated zone and the second foveated zone in each of the three separate color channels may not be aligned with respect to each other in a series of frames.

According to some embodiments, a method of realizing video pipeline implementation of dynamically multiplexed foveated rendering with late time warp and raster scan output includes rendering a foveated image that includes a foveated zone and a peripheral zone, wherein the foveated zone has a first set of image data and is rendered at a first pixel resolution and the peripheral zone has a second set of image data and is rendered at a second pixel resolution lower than the first pixel resolution and generating a control packet that includes rendering information associated with the foveated image. The method further includes time warping the foveated image for movement in a viewer's position to form a time warped image, transmitting the time warped image and the control packet to a video processor, and performing a late time warping of the time warped image to form an updated image based on the latest viewer's pose data. The method also includes packing the updated image and the control packet to form a frame, transmitting the frame to a display unit, wherein the display unit parses the control packet from the frame, decodes the control packet to obtain the rendering information, and saves the rendering information of the frame in a memory of the display unit, and projecting a display image rendered according to the rendering information.

The control packet can be decoded by a control packet decoder. The time warped image can be transmitted to the video processor via a headset link. The same control packet can be used for a series of frames. A location of the foveated zone can be dynamically changed in a series of frames. The first set of image data and the second set of image data are in rasterized form.

BRIEF DESCRIPTION OF THE DRAWINGS

FIGS. 2A-2E illustrate some example artifacts that can be caused by subsampling in FR.

FIGS. 3A-3C are spatial profiles illustrating a field of view and foveated rendering using temporal multiplexing according to some embodiments.

FIGS. 3D-3F are images illustrating native resolution, subsampling, and image blending according to an embodiment of the present invention.

FIGS. 3G-3H are text boxes illustrating subsampling and temporal multiplexing according to an embodiment of the present invention.

FIG. 9 shows an exemplary control packet to be embedded in a video frame that provides FR information for use in a video pipeline according to some embodiments.

DETAILED DESCRIPTION OF SPECIFIC EMBODIMENTS

In foveated rendering (FR), a spatial profile for a field of view (FOV) can be used to match the rendering quality to the visual acuity of human eyes. The spatial profile includes a foveated zone and one or more peripheral regions. The foveated zone would be rendered with maximum fidelity (e.g., at the native pixel resolution), while the peripheral regions would be rendered with lower resolutions. The spatial profile can be fixed within the FOV, or can be shifted based on eye gaze tracking data or based on content-estimations. Due to the inaccuracy and latency in eye gaze tracking or content-estimation, perceptual artifacts are often seen in FR.

According to some embodiments, methods of FR using temporal multiplexing and/or binocular multiplexing of spatial profiles are provided. Such methods can improve the perceived visual quality of FR and reduce visual artifacts of FR. The methods can be used without eye gaze tracking, or can be used in conjunction with eye gaze tracking. Such methods can be implemented in a video pipeline from a graphics processor to a display unit using frame-specific control packets that provide information of FR for each frame. Thus, satisfactory visual quality of FR can be achieved while saving computation power and transmission bandwidth. These methods are discussed in more detail below.

Figure 1:
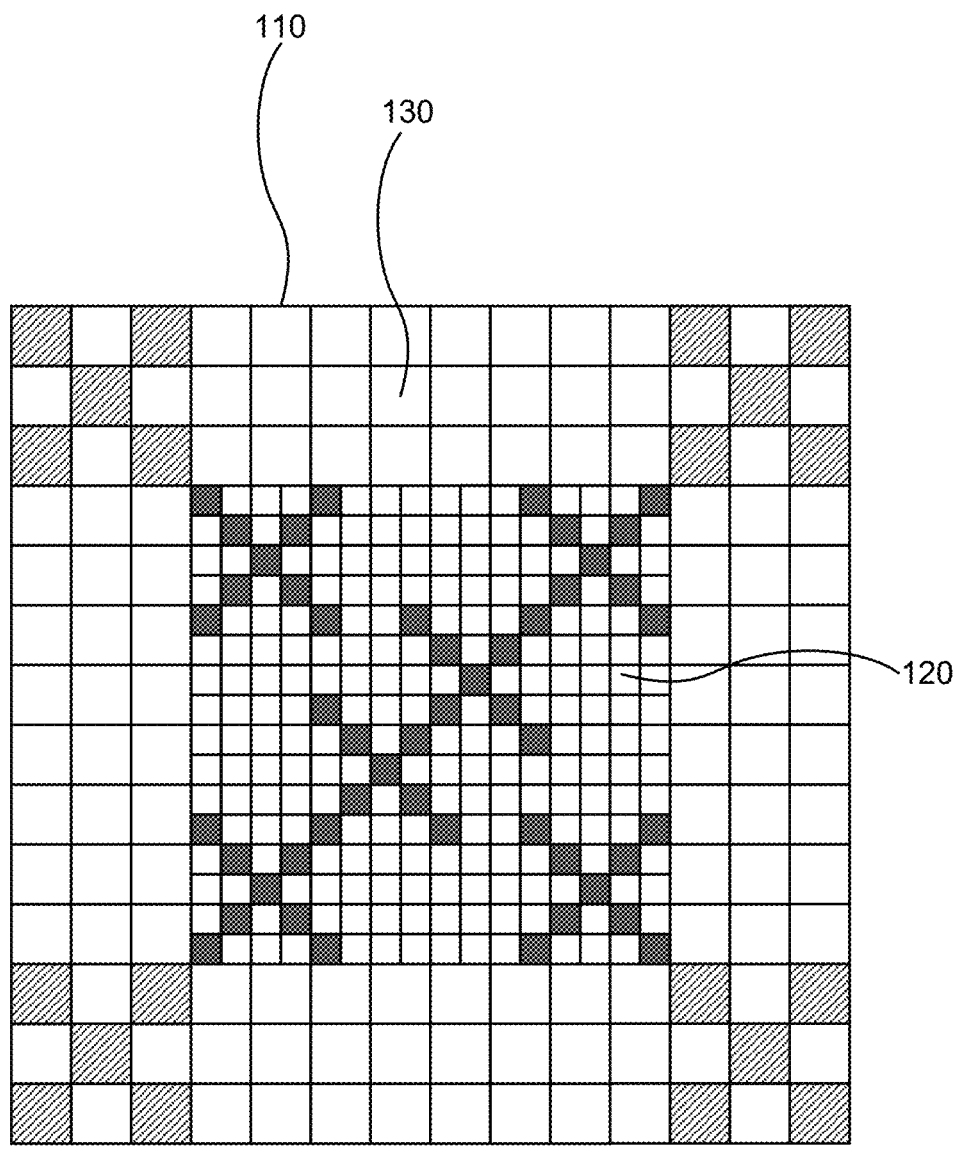
FIG. 1 is an exemplary image illustrating an implementation of foveated rendering (FR).

FIG. 1 is an exemplary image illustrating an implementation of FR. The field of view (FOV) 110 is divided into two zones: a foveated zone 120 in the central region, and a peripheral zone 130 around the foveated zone 120. The foveated zone 120 is rendered with native resolution (illustrated with finer pixel grids), whereas the peripheral zone 130 is rendered with reduced resolution (illustrated with courser pixel grids). The location of the foveated zone 120 within the FOV 110 can be determined by measuring eye fixations using eye gaze trackers, or by inferring where the viewer is looking at on the basis of content. Alternatively, the location of the foveated zone 120 can be fixed, e.g., at the center of the FOV 110, assuming that the viewer is looking at the center of the FOV 110.

The rendering pixel size in the peripheral zone 130 is often equal to an integer multiple of the pixel size in the foveated zone 120, e.g., through pixel binning or subsampling. For example, a group of m×n native pixels can be replaced with one super pixel. In the example illustrated in FIG. 1, a group of 2×2 native pixels are merged into one large pixel in the peripheral zone 130. Thus, the resolutions are halved in the peripheral zone 130 in both the horizontal and vertical dimensions compared to the resolutions in the foveated zone 120. This example is used in the discussions below.

An assumption underlying FR is that the viewer sees the reduced-resolution regions with his or her peripheral vision, where visual acuity is poor enough so that no effects of resolution reduction are perceptible. In reality, this assumption can be invalid due to eye gaze tracking errors, or because of eye movements in the fixed FR. Thus, the viewer may see some artifacts due to the subsampling in FR.

FIGS. 2A-2E illustrate some example artifacts that can be caused by subsampling. Assuming a 2×2 subsampling, a one-pixel-wide line 210 shown in FIG. 2A would become a two-pixel-wide line 220 shown in FIG. 2B. That is, the maximum spatial frequency is halved. Since adjacent pixels are combined, their luminance is averaged. Thus, the contrast is reduced, as illustrated in FIGS. 2A and 2B. Color may also be changed due to subsampling. For example, as illustrated in FIGS. 2C and 2D, a red line 230 and a green line 240 at the boundary between a red area and a green area may be combined into a wide yellow line 250. Subsampling may also reduce the legibility of fine text, as illustrated in FIG. 2E, in which the left side shows the text in native pixels and the right side shows the text in subsampled pixels.

The above artifacts can be more noticeable when the content moves as a result of the viewer's head motion or the motion of the content itself. For example, a boundary may be seen between the foveated zone and the peripheral zone, as indicated by brightness and/or contrast differences. When the content has a high contrast, for instance, white text on a black background seen with VR headsets or seen against a dark background with AR headsets, the above artifacts may be more noticeable.

According to some embodiments, methods are provided to improve the perceptual quality of images rendered by FR by reducing the noticeability of the artifacts discussed above. Instead of using a fixed spatial profile for rendering (i.e., foveated native resolution vs. peripheral reduced resolution), temporal and/or binocular multiplexing of varying spatial profiles are used for rendering. These methods are also referred to herein as temporal "dithering." The solutions can have the advantage of being computationally lightweight, and yet not requiring accurate and fast eye gaze tracking.

FIGS. 3A-3C are spatial profiles illustrating a field of view and foveated rendering using temporal multiplexing according to some embodiments. FIG. 3A shows a first spatial profile, in which a FOV 310 is divided into a first foveated zone 320 (represented by the dark pixels) and a first peripheral zone 330 (represented by the white pixels). FIG. 3B shows a second spatial profile, in which the FOV 310 is divided into a second foveated zone 340 and a second peripheral zone 350. As illustrated, the second foveated zone 340 is shifted with respect to the first foveated zone 320 in the horizontal direction (e.g., by 4 native pixels in the X direction).

According to some embodiments, the first spatial profile and the second spatial profile are temporally multiplexed in a sequence of frames. For instance, the first spatial profile can be used for rendering odd frames, and the second spatial profile can be used for rendering even frames. In this fashion, the foveated zone is dynamically moved from frame to frame in a sequence of frames. Thus, for a region of the FOV 310 where the first foveated zone 320 and the second foveated zone 340 overlap (e.g., the dark middle rows illustrated in FIG. 3C), images rendered at the native resolution are presented at all times. For a region of the first foveated zone 320 that does not overlap with the second foveated zone 340 or a region of the second foveated zone 340 that does not overlap with the first foveated zone 320 (e.g., the grey rows illustrated in FIG. 3C), native-resolution images and subsampled images are presented alternatively from frame to frame.

Assuming that the display has a high-enough refresh rate (e.g., 120 Hz), native-resolution images and subsampled images may be blended into one as perceived by the viewer. The blending of the native-resolution images and the subsampled images can help to restore high-spatial frequencies and luminance contrast in the viewer's visual perception. FIGS. 3D-3F illustrate an example.

FIGS. 3D-3F are images illustrating native resolution, subsampling, and image blending according to an embodiment of the present invention. FIG. 3D shows a native resolution image that includes a one-pixel-wide line 360. FIG. 3E shows a subsampled image in which the one-pixel-wide line 360 becomes a two-pixel-wide line 370. FIG. 3F shows a result of blending the two images shown in FIGS. 3D and 3E, as may be perceived by a viewer. As illustrated in FIG. 3F, the high spatial resolution and contrast of the native resolution image are somewhat restored.

FIGS. 3G-3H are text boxes illustrating subsampling and temporal multiplexing according to an embodiment of the present invention. FIG. 3G shows some text in a subsampled image. FIG. 3H shows the text in which a native resolution image and a subsampled image are multiplexed. As illustrated, the legibility of the text in FIG. 3H is improved as compared to FIG. 3G. Thus, in the example illustrated in FIGS. 3A-3C, by temporally multiplexing the first spatial profile shown in FIG. 3A and the second spatial profile shown in FIG. 3B, the effective foveated zone (e.g., the combined dark and grey area in FIG. 3C) can be enlarged as compared to the foveated zone 320 or 340 in each individual spatial profile.

According to various embodiments, the location of the foveated zone can be spatially shifted between consecutive frames horizontally (e.g., in the X direction), or vertically (e.g., in the Y direction), or in both directions (e.g., combination of X and Y directions). In addition, the direction as well as the amount of the spatial shift can be varied dynamically. The frame rate may be limited by the capability of the display (e.g., a spatial light modulator or SLM). For example, the frame rate can be 120 Hz or higher. In some embodiments, the foveated zone can be spatially shifted to a set of predetermined locations in a fixed order or a random order, to cover as much of the FOV 310 as possible. Therefore, a viewer may perceive high quality images in the entire FOV, even when the viewer's eye gaze changes.

Figure 4:
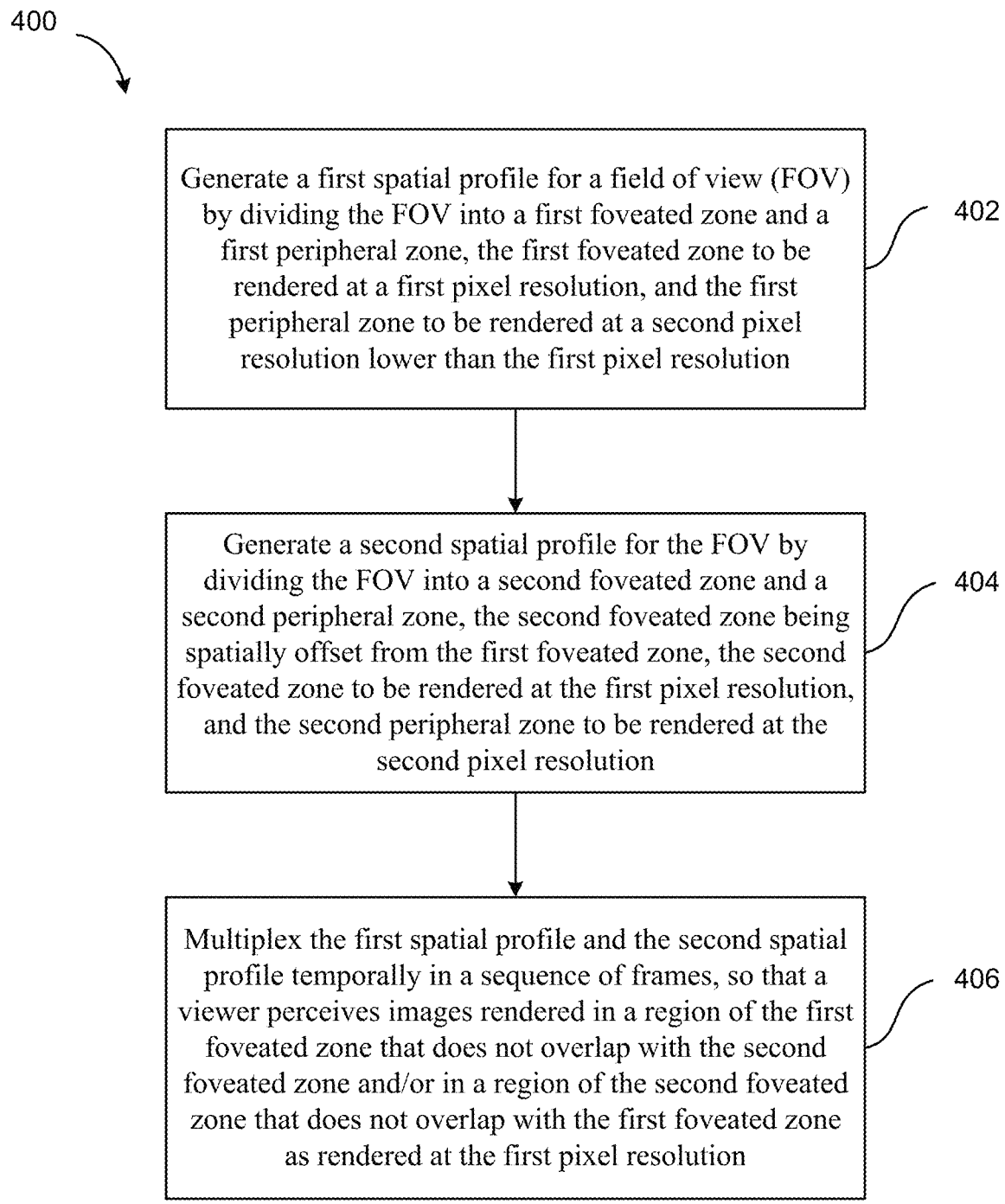
FIG. 4 shows a simplified flowchart illustrating a method of generating foveated rendering using temporal multiplexing according to some embodiments.

FIG. 4 shows a simplified flowchart illustrating a method 400 of generating foveated rendering using temporal multiplexing according to some embodiments.

The method 400 includes, at 402, generating a first spatial profile for an FOV by dividing the FOV into a first foveated zone and a first peripheral zone. The first foveated zone will be rendered at a first pixel resolution, and the first peripheral zone will be rendered at a second pixel resolution lower than the first pixel resolution.

The method 400 further includes, at 404, generating a second spatial profile for the FOV by dividing the FOV into a second foveated zone and a second peripheral zone. The second foveated zone is spatially offset from the first foveated zone. The second foveated zone will be rendered at the first pixel resolution, and the second peripheral zone will be rendered at the second pixel resolution.

The method 400 further includes, at 406, multiplexing the first spatial profile and the second spatial profile temporally in a sequence of frames, so that a viewer perceives images rendered in a region of the first foveated zone that does not overlap with the second foveated zone and/or in a region of the second foveated zone that does not overlap with the first foveated zone as rendered at the first pixel resolution.

It should be appreciated that the specific steps illustrated in FIG. 4 provide a particular method of generating foveated rendering according to some embodiments. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

Figures 5A, 5B, 5C:
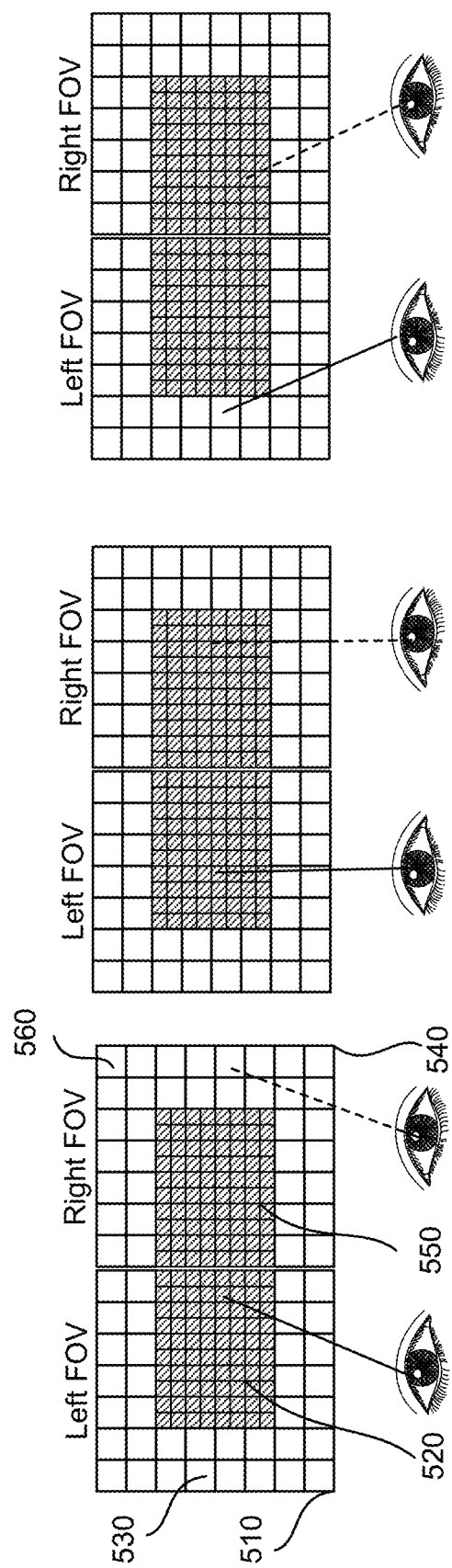
FIGS. 5A-5D are spatial profiles illustrating a left field of view and a right field of view for foveated rendering using binocular multiplexing according to some embodiments.

According to some embodiments, additionally or alternatively, binocular multiplexing can be applied to reduce perceptual artifacts. FIGS. 5A-5D illustrate spatial profiles illustrating a left field of view and a right field of view for foveated rendering using binocular multiplexing according to some embodiments. Referring to FIG. 5A, in a first spatial profile, the field of view (FOV) for the left eye 510 is divided into a first foveated zone 520 (represented by the grey pixels) and a first peripheral zone 530 (represented by the white pixels). In a second spatial profile, the FOV for the right eye 540 is divided into a second foveated zone 550 and a second peripheral zone 560. It is assumed that the FOV for the left eye 510 and the FOV for the right eye 540 are identical. As illustrated, instead of being fixed in the center of the FOV, the first foveated zone 520 is shifted toward the right, and the second foveated zone 550 is shifted toward the left.

Referring to FIG. 5B, if the viewer's eye fixation lands at the center of the FOV where the first foveated zone 520 and the second foveated zone 550 overlap, the viewer may see native-resolution images in both eyes in his or her central vision. Referring to FIG. 5A, if the viewer's eye fixation lands on the right side of the FOV, the viewer may see native-resolution images in the left eye and subsampled images in the right eye in his or her central vision. Referring to FIG. 5C, if the viewer's eye fixation lands on the left side of the FOV, the viewer may see native-resolution images in the right eye and subsampled images in the left eye in his or her central vision.

Figure 5D:
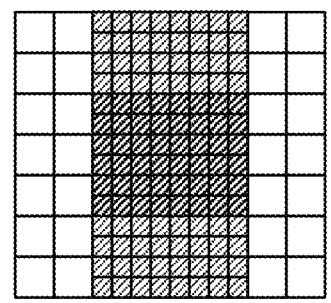

FIG. 5D illustrates the effective spatial profile. When looking at the region represented by dark pixels, the viewer may see native-resolution images in both eyes. When looking at the regions represented by grey pixels, the viewer may see native-resolution images in only one of the eyes. As illustrated in FIG. 5D, the combined region (represented by the grey and dark pixels) at which native-resolution images are seen by at least one eye is larger than the foveated zone 520 or 550 in each individual spatial profile. Thus, the artifacts due to subsampling can be suppressed. According to various embodiments, the location of the foveated zone 520 and 550 can be shifted horizontally (e.g., in the X direction), or vertically (e.g., in the Y direction), or in both directions (e.g., combination of X and Y directions).

Figure 6A:
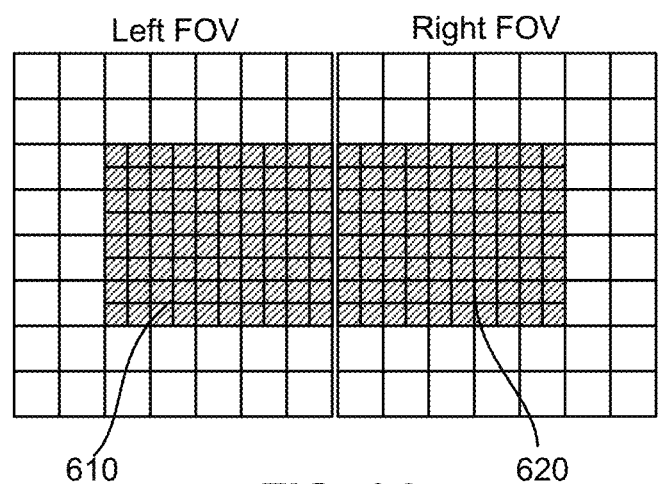
FIGS. 6A-6C are spatial profiles illustrating a left field of view and a right field of view for foveated rendering using binocular multiplexing in combination with temporal multiplexing according to some embodiments.
Figure 6B:
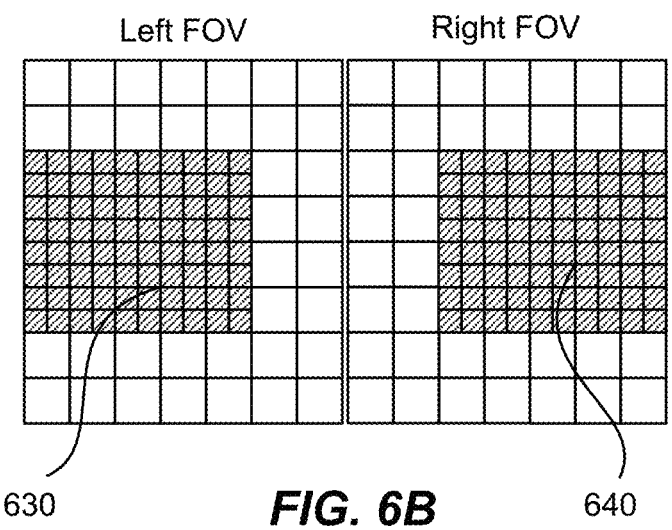
Figure 6C:
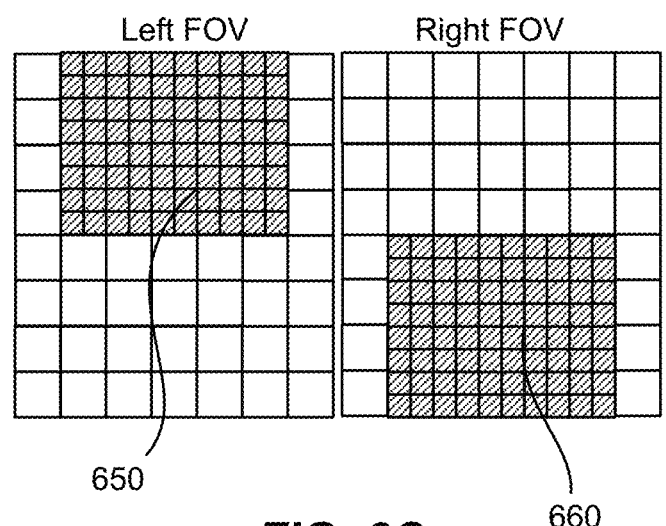

According to some embodiments, binocular multiplexing can be combined with temporal multiplexing. FIGS. 6A-6C are spatial profiles illustrating a left field of view and a right field of view for foveated rendering using binocular multiplexing in combination with temporal multiplexing according to some embodiments. Referring to FIG. 6A, in a first frame, a first spatial profile for the left FOV can have the foveated zone 610 shifted toward the right, and a second spatial profile for the right FOV can have the foveated zone 620 shifted toward the left. Referring to FIG. 6B, in a second frame, a third spatial profile for the left FOV can have the foveated zone 630 shifted toward the left, and a fourth spatial profile for the right FOV can have the foveated zone 640 shifted toward the right. In some embodiments, in a sequence of frames, the first frame as shown in FIG. 6A can be for every odd frame, and the second frame as shown in FIG. 6B can be for every even frame.

Referring to FIG. 6C, in a third frame, a fifth spatial profile for the left FOV can have the foveated zone 650 shifted upward, and a sixth spatial profile for the right FOV can have the foveated zone 660 shifted downward. In some embodiments, the direction as well as the amount of the spatial shift can be varied dynamically. For example, the foveated zone for both the left FOV and the right FOV can be spatially shifted to a set of predetermined locations in a fixed order or a random order, to cover as much of the FOV as possible. Therefore, a viewer may perceive high quality images in the entire FOV, while saving bandwidth significantly. The movement of the foveated zones can be calculated using the minimal and maximum possible interpupillary distances (IPDs) to ensure that good visual results can be achieved for the targeted viewers.

According to some embodiments, the methods of temporal multiplexing and binocular multiplexing of spatial profiles can be applied to various types of FR implementations, including, e.g., fixed FR, FR with eye gaze tracking, or content-based FR. When applied to FR with eye gaze tracking, the methods described herein can effectively extend the foveated region and hence reduce the artifacts produced by inaccurate eye gaze tracking. When applied to content-based FR, the methods described herein can reduce the artifacts due to prediction errors. When applied to fixed FR, the methods described herein can help make a smooth transition in visual quality from the highest resolution in the foveated region, to a multiplexed resolution in the near-periphery, and to the subsampled resolution in the far-periphery.

Figure 7:
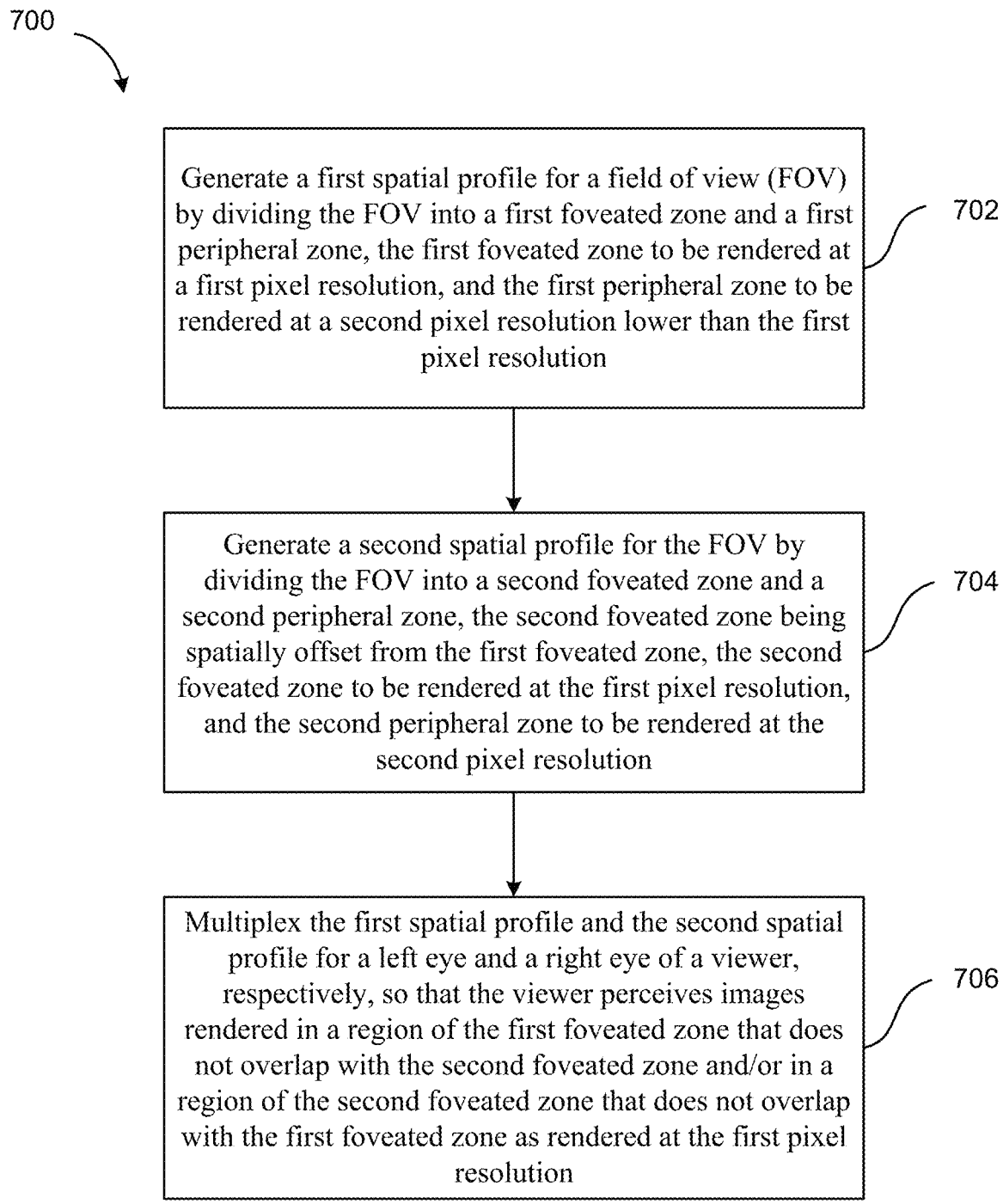
FIG. 7 shows a simplified flowchart illustrating a method of generating foveated rendering using binocular multiplexing according to some embodiments.

FIG. 7 shows a simplified flowchart illustrating a method 700 of generating foveated rendering using binocular multiplexing according to some embodiments.

The method 700 includes, at 702, generating a first spatial profile for an FOV by dividing the FOV into a first foveated zone and a first peripheral zone. The first foveated zone will be rendered at a first pixel resolution, and the first peripheral zone will be rendered at a second pixel resolution lower than the first pixel resolution.

The method 700 further includes, at 704, generating a second spatial profile for the FOV by dividing the FOV into a second foveated zone and a second peripheral zone. The second foveated zone is spatially offset from the first foveated zone. The second foveated zone will be rendered at the first pixel resolution, and the second peripheral zone will be rendered at the second pixel resolution.

The method 700 further includes, at 706, multiplexing the first spatial profile and the second spatial profile for a left eye and a right eye of a viewer, respectively, so that the viewer perceives images rendered in a region of the first foveated zone that does not overlap with the second foveated zone and/or in a region of the second foveated zone that does not overlap with the first foveated zone as rendered at the first pixel resolution.

It should be appreciated that the specific steps illustrated in FIG. 7 provide a particular method of generating foveated rendering according to some embodiments. Other sequences of steps may also be performed according to alternative embodiments. For example, alternative embodiments of the present invention may perform the steps outlined above in a different order. Moreover, the individual steps illustrated in FIG. 7 may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

Figure 8:
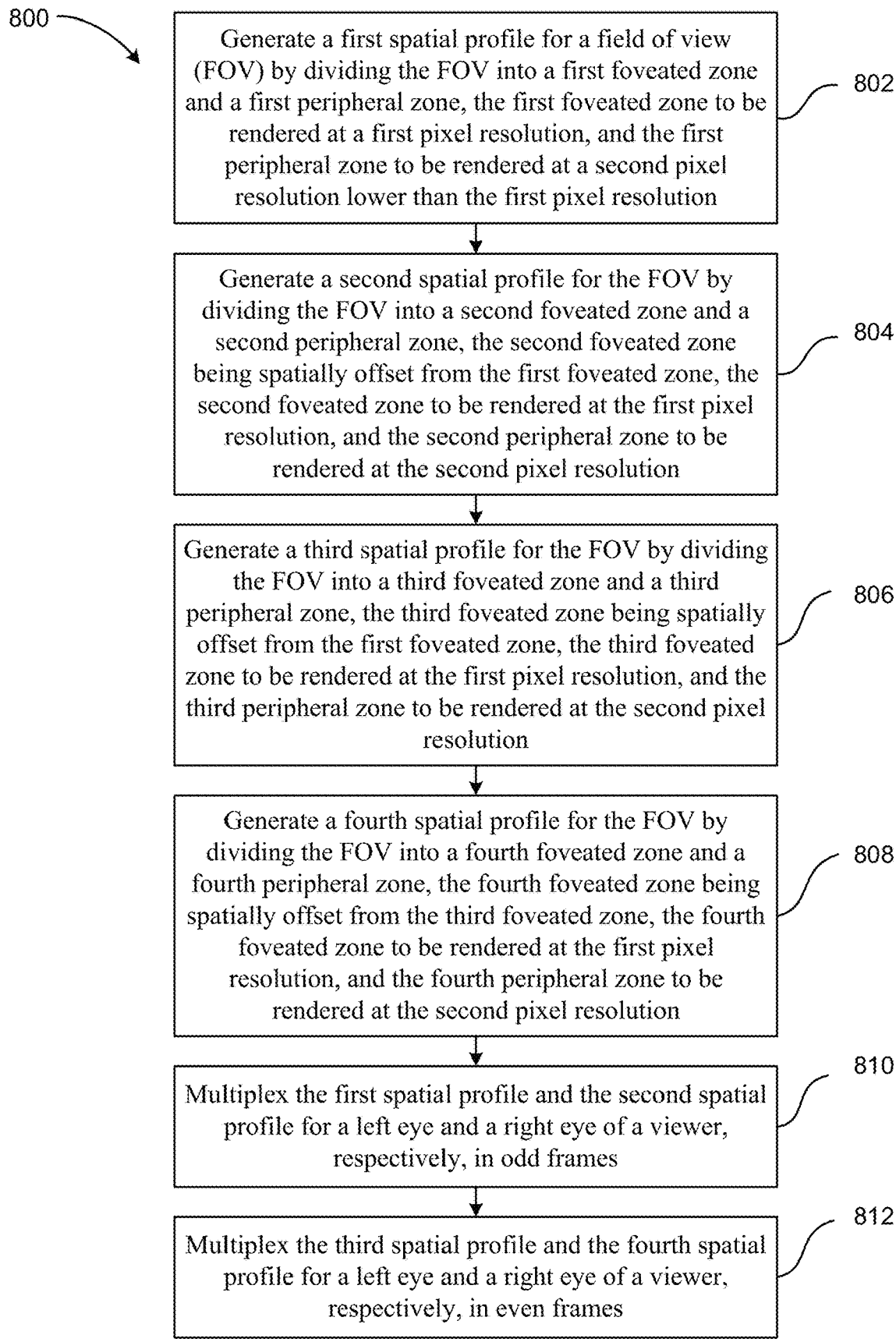
FIG. 8 shows a simplified flowchart illustrating a method of generating foveated rendering using a combination of temporal multiplexing and binocular multiplexing according to some embodiments.

FIG. 8 shows a simplified flowchart illustrating a method 800 of generating foveated rendering using a combination of temporal multiplexing and binocular multiplexing according to some embodiments.

The method 800 includes, at 802, generating a first spatial profile for an FOV by dividing the FOV into a first foveated zone and a first peripheral zone. The first foveated zone will be rendered at a first pixel resolution, and the first peripheral zone will be rendered at a second pixel resolution lower than the first pixel resolution.

The method 800 further includes, at 804, generating a second spatial profile for the FOV by dividing the FOV into a second foveated zone and a second peripheral zone. The second foveated zone is spatially offset from the first foveated zone. The second foveated zone will be rendered at the first pixel resolution, and the second peripheral zone will be rendered at the second pixel resolution.

The method 800 further includes, at 806, generating a third spatial profile for the FOV by dividing the FOV into a third foveated zone and a third peripheral zone. The third foveated zone is spatially offset from the first foveated zone. The third foveated zone will be rendered at the first pixel resolution, and the third peripheral zone will be rendered at the second pixel resolution.

The method 800 further includes, at 808, generating a fourth spatial profile for the FOV by dividing the FOV into a fourth foveated zone and a fourth peripheral zone. The fourth foveated zone is spatially offset from the third foveated zone. The fourth foveated zone will be rendered at the first pixel resolution, and the fourth peripheral zone will be rendered at the second pixel resolution.

The method 800 further includes, at 810, multiplexing the first spatial profile and the second spatial profile for a left eye and a right eye of a viewer, respectively, in odd frames.

The method 800 further includes, at 812, multiplexing the third spatial profile and the fourth spatial profile for a left eye and a right eye of a viewer, respectively, in even frames.

It should be appreciated that the specific steps illustrated in FIG. 8 provide a particular method of generating foveated rendering according to some embodiments. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

The methods of FR rendering described herein can be implemented in the hardware and/or software pipeline in various ways. For example, they can be implemented in the designs of AR/VR systems through firmware or middleware. Such implementations can be transparent to applications. Alternatively, they can be implemented in existing AR/VR systems through software in the operating system (OS) or individual applications.

According to some embodiments, resource savings can be realized through the entire pipeline from rendering to display. A graphics driver (e.g., a graphics processing unit or GPU) can first generate both the low resolution and high resolution images for each frame and pack them to minimize the video payload. The locations of the low resolution image and the high resolution image can be assumed to change every frame. A control packet can be embedded within the video frame that provides frame-specific information of the FR, including the pixel indexing of the foveated zone. The information provided by the control packet can assist a display unit (e.g., an SLM ASIC) to unpack the image data for each frame.

FIG. 9 shows an exemplary control packet according to some embodiments. The control packet can be embedded in a video frame generated by a GPU. The control packet can include information such as whether the FR mode is enabled, the ratio of downsampling (e.g., 4:1, 9:1, 16:1, and the like), the indices of the start row and the start column of the foveated regions. The control packet can serve as a map for the display unit (e.g., by a SLM ASIC) to unpack the image data in the video frame. The ratio of downsampling can be dynamically changed from frame to frame. For example, the ratio can be 16:1 for most frames, and be changed into 4:1 for those frames with text content.

In some embodiments, each video frame can include color channels for the three primary colors (e.g., red, green, and blue). Each color channel can independently have the FR mode enabled or disabled. For example, since the human eye has the strongest perception of green, it may be advantageous to have the green content in full resolution in the entire frame, and apply FR only to the red content and blue content. The foveated zone for each color channel can have its own ratio of downsampling, size, and locations with indices of start row and start column. For example, green content can have a lower ratio of downsampling than that of red and blue. Also, the foveated zones for the three color channels do not need to be aligned with respect to each other.

It should be appreciated that the information that may be included in a control packet is not limited to the specific information discussed above. Any information or factors that may affect image rendering, processing, display and the like may be included in the control packet.

Figure 10:
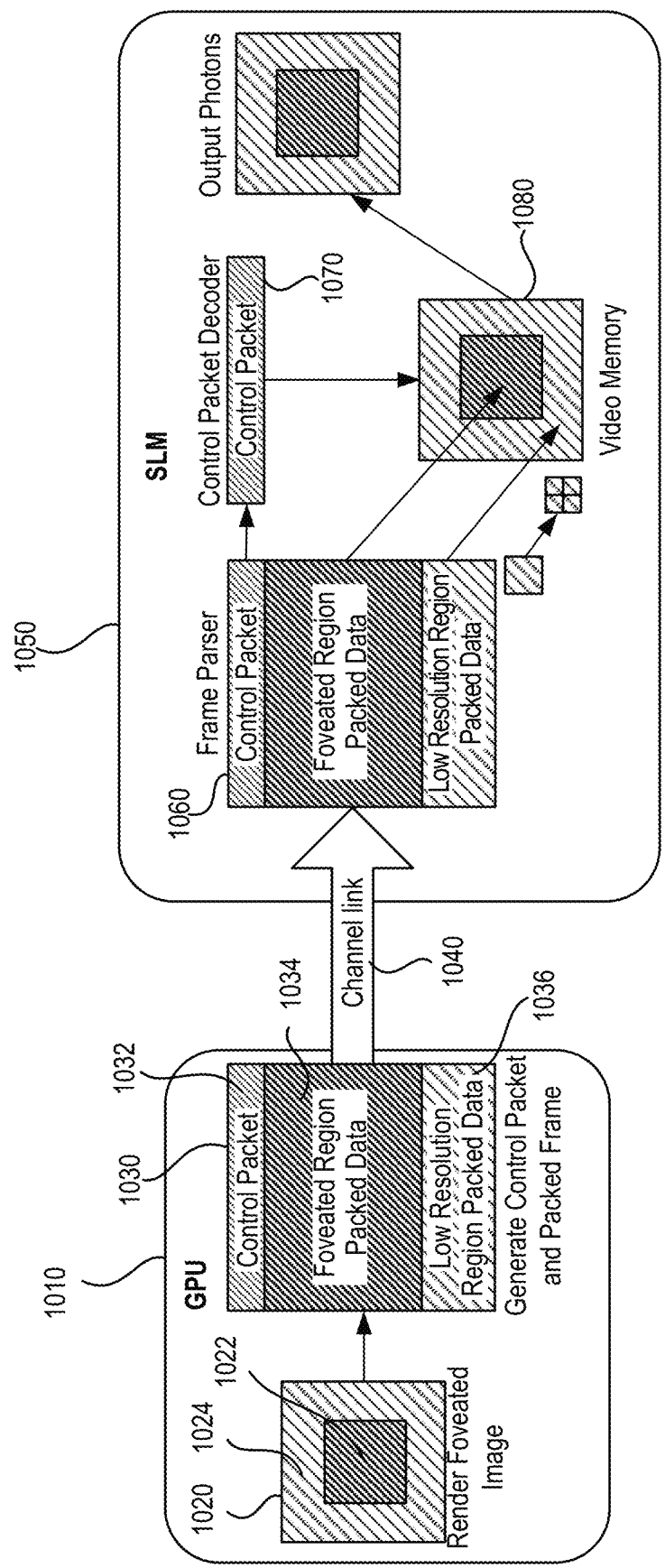
FIG. 10 shows a block diagram of an exemplary video pipeline for dynamically multiplexed FR according to some embodiments.

FIG. 10 shows a block diagram of an exemplary video pipeline implementation of dynamically multiplexed foveated rendering according to some embodiments. An image 1020 (e.g., a video frame) can be rendered at the GPU 1010. The image 1020 includes a foveated zone 1022 rendered at a high resolution and a peripheral zone 1024 rendered at a low resolution. The image data (including the high resolution image data for the foveated zone 1022 and the low resolution image data for the peripheral zone 1024) are packed into a video frame 1030. For example, the high resolution image data can be packed into a first image block 1034, and the low resolution image data can be packed into a second image block 1036.

A control packet 1032 is then concatenated with the first image block 1034 and the second image block 1036. The control packet 1032 can include information about the FR rendering (e.g., as illustrated in FIG. 9). The video frame 1030 can be sent over to a display unit 1050 (e.g., an SLM ASIC) via a channel link 1040. The packing of the video frame with the control packet 1032 can significantly reduce the payload and the data rate required, thereby minimizing the bandwidth and power on the channel link 1040.

The display unit 1050 can use a frame parser 1060 (e.g., a decoder) to parse the control packet 1032 from the first image block 1034 and the second image block 1036. For example, the control packet 1032 can be in the first row (e.g., row zero) of the video frame 1030. A control packet decoder 1070 can decode the control packet 1032. The information provided by the control packet 1032 can then be used to map the image data in the first image block 1034 and the second image block 1036 to the foveated zone and the peripheral zone, respectively, in the video memory 1080. For the low resolution region, a large pixel can be mapped to several native pixels of the display (e.g., to four native pixels if the subsampling ratio is 4:1). The display unit 1050 performs this decoding process for each frame. The display unit 1050 then projects the image saved in the video memory 1080 to a viewer (e.g., outputting photons via an SLM). In some embodiments, time stamps can also be included in the video frame 1030 to help with synchronization and managing latency, as well as partial screen refresh tasks, blank modes, and the like.

Figure 11:
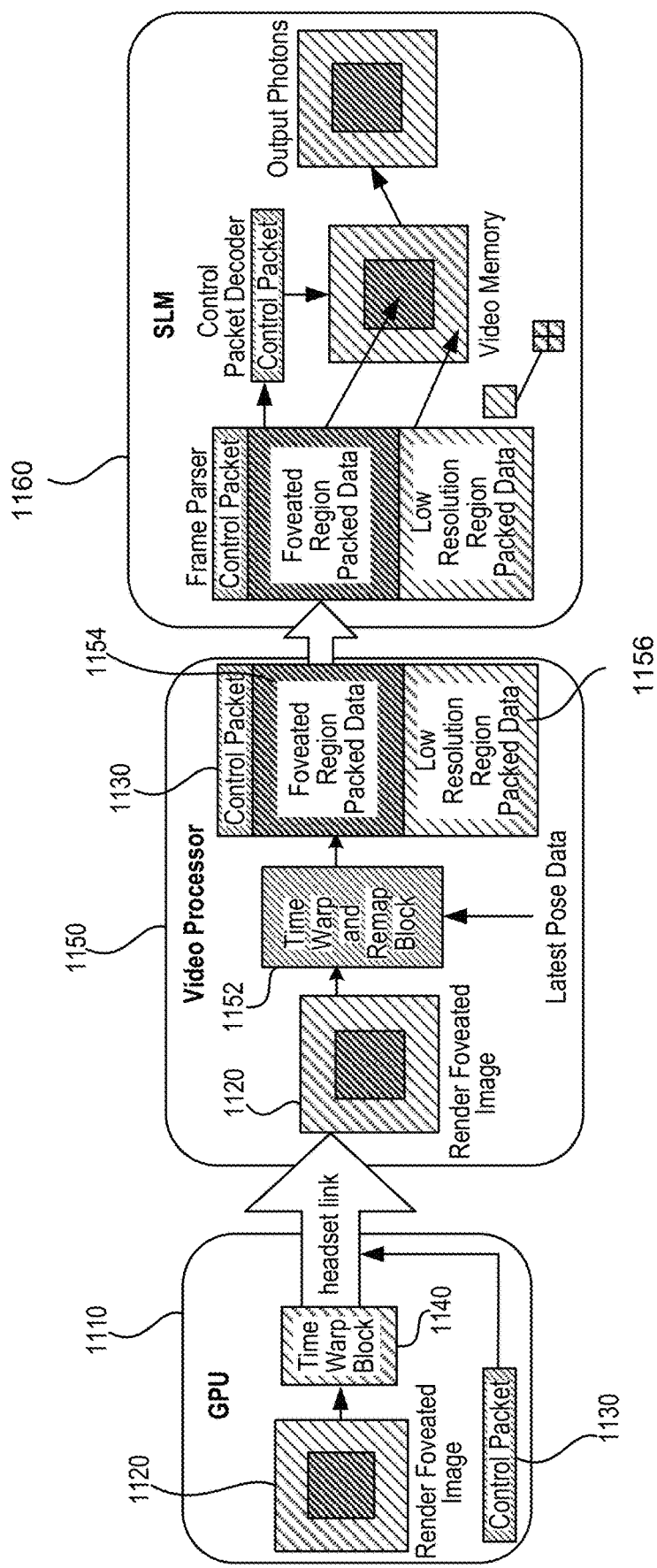
FIG. 11 shows a block diagram of an exemplary video pipeline for dynamically multiplexed FR that includes time warp according to some embodiments.

According to some embodiments, a GPU renders a foveated image and generates an associated control packet. A time warp function can be performed on the image data based on a latest pose prediction from a computer vision processor to provide an image to a display unit to reflect the viewer's point of view based on the latest pose prediction. According to some embodiments, the time warp may be performed prior to sending the image data and the control packet to the display unit. As illustrated in FIG. 11, time warping may be performed at time warp block 1140 before the image data and the control packet is sent to video processor 1150 as well as at time warp and remap block 1152 of video processor 1150. Thus, in some embodiments, the time warp may be performed by a computer vision processor coupled to the display unit. The foveated image is then sent to a wearable video processor, while the control packet is sent over a secondary data channel. The video processor then performs a late time warp (e.g., using the latest pose data from a sensor suite of the wearable device) and reformats the foveated image, with a foveated region and a low resolution region. This method can work well for a global refresh SLM that is capable of unpacking the image before display. For a color sequential display, red, green, and blue packed images can be generated and sent separately.

FIG. 11 shows a block diagram of an exemplary video pipeline for dynamically multiplexed foveated rendering that includes time warp according to some embodiments. A GPU 1110 generates a foveated image 1120 and an associated control packet 1130 (e.g., as illustrated in FIG. 9). A time warp block 1140 performs a time warp function on the foveated image 1120 to account for movement in the viewer's position. The image data and the control packet 1130 are then sent to a video processor 1150 of a wearable device via a headset link.

At the video processor 1150, a time warp and remap block 1152 can perform a late time warp using the latest pose data (e.g., from a sensor suite of the wearable device). For example, in cases in which there is significant head motion, the latest pose data can be used to update the boundaries. The time warp and remap block 1152 can also remap the foveated image 1120 into a foveated region data block 1154 and a low resolution region data block 1156. The control packet 1130 can be concatenated with the foveated region data block 1154 and the low resolution region data block 1156 to form a video frame, to be sent to the display unit 1160 (e.g., an SLM ASIC). The display unit 1160 can unpack the video frame using the control packet in a manner similar to that of the display unit 1050 illustrated in FIG. 10 and discussed above.

Figure 12:
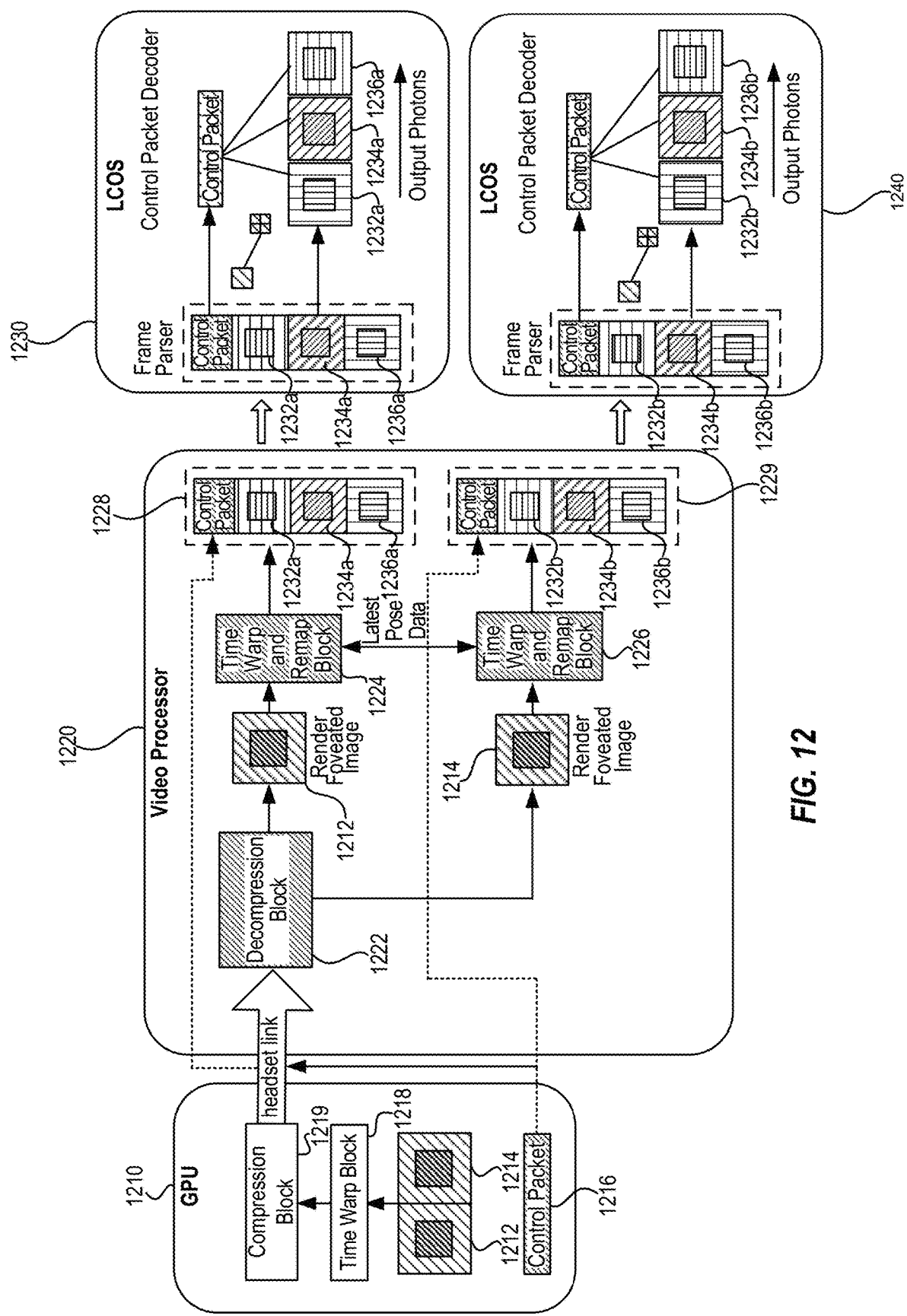
FIG. 12 shows a block diagram of an exemplary video pipeline for dynamically multiplexed foveated rendering that includes time warp configured for a sequential color display according to some embodiments.
Figure 13:
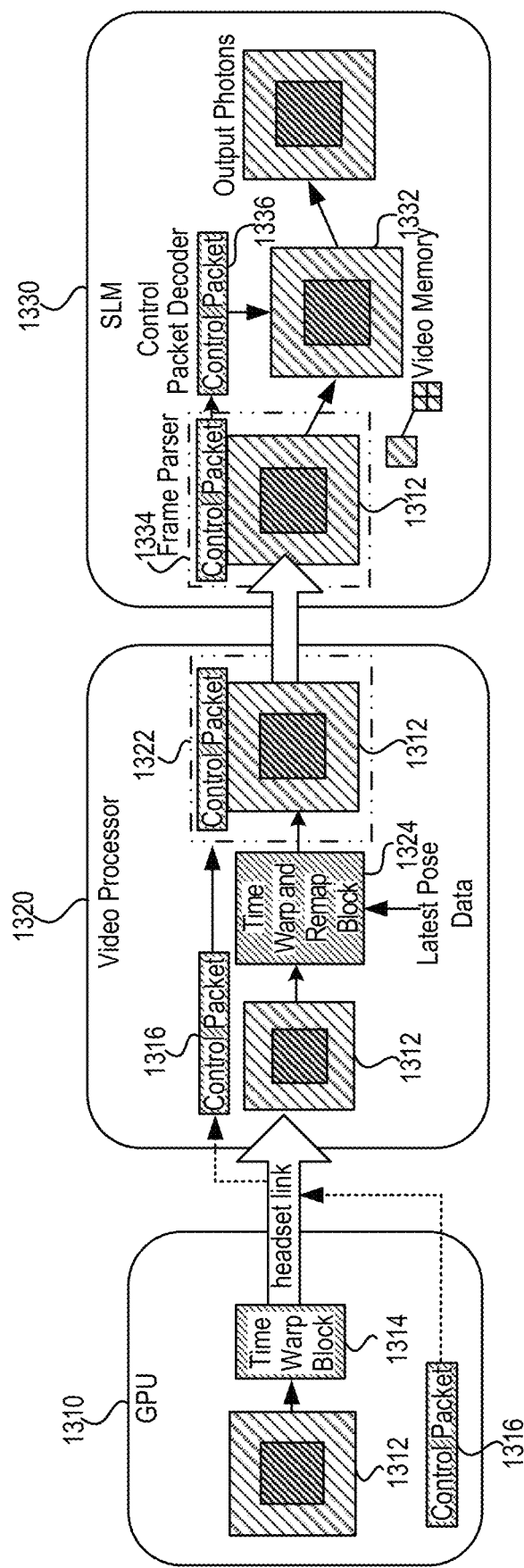
FIG. 13 shows a block diagram of an exemplary video pipeline for dynamically multiplexed foveated rendering with late time warp and raster scan output according to some embodiments.

FIG. 12 shows a block diagram of an exemplary video pipeline for dynamically multiplexed foveated rendering that includes time warp configured for a sequential color display according to some embodiments. The GPU 1210 renders a first foveated image 1212 for the left eye and a second foveated image 1214 for the right eye. An associated control packet 1216 is generated that provides information of the FR (e.g., as illustrated in FIG. 9) for both the first foveated image 1212 and the second foveated image 1214. A time warp block 1218 performs a time warp function on the first foveated image 1212 and the second foveated image 1214. A compression block 1219 performs compression of the image data. The compressed image data and the control packet 1216 are then sent to the video processor 1220 at the wearable device via a headset link.

At the video processor 1220, a decompression block 1222 decompresses the image data and recovers the first foveated image 1212 and the second foveated image 1214. A first time warp and remap block 1224 performs time warp on the first foveated image 1212 based on the latest pose data. The first time warp and remap block 1224 also maps the first foveated image 1212 into three separate color channels (e.g., red 1232a/1232b, green 1234a/1234b, and blue 1236a/1236b). The three color channels (i.e., 1232a, 1234a, and 1236a), along with the control packet, are packed as a first video frame 1228 to be sent to a first display 1230 (e.g., an LCOS display) for the left eye. A second time warp and remap block 1226 performs time warp on the second foveated image 1214 based on the latest pose data. The second time warp and remap block 1226 also maps the second foveated image 1214 into three separate color channels (i.e., 1232b, 1234b, and 1236b). The three color channels, along with the control packet, are packed as a second video frame 1229 to be sent to a second display 1240 (e.g., an LCOS display) for the right eye.

The first display 1230 can unpack the first video frame 1228 using the control packet in a manner similar to that of the display unit 1050 illustrated in FIG. 10 and discussed above. In this case, the image data for each of the three color channels 1232a, 1234a, and 1236a is saved in a video memory, to be projected to the viewer's left eye. As discussed above, each of the three color channels 1232a, 1234a, and 1236a can have its independent foveated zone, downsampling ratio, and the like. The foveated zones for the three color channels 1232a, 1234a, and 1236a do not need to be aligned with respect to each other. In some embodiments, the three color channels 1232a, 1234a, and 1236a can be displayed to the viewer sequentially. The second display 1240 can unpack the second video frame 1229 in a similar manner.

For rolling shutter type of displays, image data may be packed differently so as to keep it in a rasterized form. FIG.

13 shows a block diagram of an exemplary video pipeline for dynamically multiplexed foveated rendering with late time warp and raster scan output according to some embodiments. A foveated image 1312 is rendered at the GPU 1310. A time warp block 1314 performs a time warp function to the foveated image 1312. A control packet 1316 that includes information about the FR rendering (e.g., as illustrated in FIG. 9) can be created for the foveated image 1312. The image data and the control packet 1316 are sent to a video processor 1320 of a wearable device via a headset link.

At the video processor 1320, a time warp and remap block 1324 can perform a late time warp to the foveated image using the latest pose data (e.g., from a sensor suite of the wearable device). The time warped image and the control packet 1316 are packed together as a video frame 1322, which is then sent to the display unit 1330.

At the display unit 1330, a frame parser 1334 can parse the control packet 1316 from the foveated image 1312. A control packet decoder 1336 can decode the control packet 1316 accompanying the foveated image 1312. The information provided by the control packet 1316 can then be used to map the foveated image 1312 to the video memory 1332. For example, a large pixel in the low resolution region can be mapped to several native pixels of the display (e.g., to four native pixels if the subsampling ratio is 4:1). The display unit 1050 can then project the image saved in the video memory 1332 to a viewer (e.g., outputting photons via an SLM). As the foveated rendering can be changed dynamically from frame to frame, the display unit 1330 uses the FR information provided in the control packet 1316 for each frame, so as to ensure correct mapping.

For rolling shutter type of displays, the foveated image 1312 is kept in the rasterized form throughout the pipeline, so that the image data can be scanned out as it is scanned in. There would be no need to wait for the entire frame to be received. Thus, the video memory 1332 can be a relatively small line buffer for feeding out the newly arrived image data; there is no need for a big buffer to keep the entire frame. Also, the latency can be kept relatively low.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of generating foveated rendering for a display, the method comprising:
   generating a first spatial profile for a field of view (FOV) of the display by dividing the FOV into a first foveated zone and a first peripheral zone, the first foveated zone including first pixels rendered at a first pixel resolution, and the first peripheral zone including second pixels rendered at a second pixel resolution lower than the first pixel resolution, wherein the first foveated zone includes a first region including a subset of the first pixels and a second region including a remainder of the first pixels;
   generating a second spatial profile for the FOV of the display by dividing the FOV into a second foveated zone and a second peripheral zone, the second foveated zone being spatially offset from the first foveated zone, the second foveated zone including third pixels rendered at the first pixel resolution, and the second peripheral zone including fourth pixels rendered at the second pixel resolution, wherein the second foveated zone includes a third region including a subset of the third pixels and a fourth region including a remainder of the third pixels; and
   multiplexing the first spatial profile and the second spatial profile temporally in a sequence of frames, so that a viewer perceives images rendered in the first region of the first foveated zone that does not overlap with the second foveated zone and/or in the third region of the second foveated zone that does not overlap with the first foveated zone.

2. The method of claim 1 wherein the first foveated zone and the second foveated zone partially overlap with each other.

3. The method of claim 1 wherein the sequence of frames has a frame frequency of about 120 Hz.

4. The method of claim 1 wherein a ratio between the first pixel resolution and the second pixel resolution is 2:1 in each of two orthogonal directions.

5. The method of claim 1 wherein the second foveated zone is spatially offset from the first foveated zone in a first direction, in a second direction orthogonal to the first direction, or in both the first direction and the second direction.

6. The method of claim 5 wherein a spatial offset between the second foveated zone and the first foveated zone is dynamically changed in a series of frames.

7. The method of claim 6 wherein the dynamic changing of the spatial offset between the second foveated zone and the first foveated zone follows a pattern.

8. The method of claim 1 wherein each of the first spatial profile and the second spatial profile includes three sub spatial profiles for each of three primary colors, and wherein at least one of the three sub spatial profiles is to be rendered at the second pixel resolution for an entirety of the FOV.

9. The method of claim 1 wherein the first foveated zone or the second foveated zone is set at a predetermined location in the FOV of the display.

10. The method of claim 9 wherein the predetermined location of the first foveated zone or the second foveated zone is determined based on a measurement of a viewer's eye positions and eye movements.

11. A method of generating foveated rendering for a display, the method comprising:
   generating a first spatial profile for a field of view (FOV) of the display by dividing the FOV into a first foveated zone and a first peripheral zone, the first foveated zone including first pixels rendered at a first pixel resolution, and the first peripheral zone including second pixels rendered at a second pixel resolution lower than the first pixel resolution, wherein the first foveated zone includes a first region including a subset of the first pixels and a second region including a remainder of the first pixels;
   generating a second spatial profile for the FOV of the display by dividing the FOV into a second foveated zone and a second peripheral zone, the second foveated zone being spatially offset from the first foveated zone, the second foveated zone including third pixels rendered at the first pixel resolution, and the second peripheral zone including fourth pixels rendered at the second pixel resolution, wherein the second foveated zone includes a third region including a subset of the third pixels and a fourth region including a remainder of the third pixels; and
   multiplexing the first spatial profile and the second spatial profile for a left eye and a right eye of a viewer viewing the display, respectively, so that the viewer perceives images rendered in the first region of the first foveated zone that does not overlap with the second foveated zone and/or in the third region of the second foveated zone that does not overlap with the first foveated zone.

12. The method of claim 11 wherein the first foveated zone and the second foveated zone partially overlap with each other.

13. The method of claim 11 wherein a sequence of frames has a frame frequency of about 120 Hz.

14. The method of claim 11 wherein a ratio between the first pixel resolution and the second pixel resolution is 2:1 in each of two orthogonal directions.

15. The method of claim 11 wherein the second foveated zone is spatially offset from the first foveated zone in a first direction, in a second direction orthogonal to the first direction, or in both the first direction and the second direction.

16. The method of claim 15 wherein the spatial offset between the second foveated zone and the first foveated zone is dynamically changed in a sequence of frames.

17. The method of claim 16 wherein the dynamic changing of the spatial offset between the second foveated zone and the first foveated zone follows a pattern.

18. The method of claim 11 wherein each of the first spatial profile and the second spatial profile includes three sub spatial profiles for each of three primary colors, and wherein at least one of the three sub spatial profiles is to be rendered at the second pixel resolution for an entirety of the FOV of the display.

19. The method of claim 11 wherein the first foveated zone or the second foveated zone is set at a predetermined location in the FOV of the display.

20. The method of claim 19 wherein the predetermined location of the first foveated zone or the second foveated zone is determined based on a measurement of a viewer's eye positions and eye movements.

* * * * *